United States Patent

Umemura et al.

[11] 4,177,161
[45] Dec. 4, 1979

[54] CATALYTIC OXIDATIVE PROCESS FOR PRODUCING MALEIC ANHYDRIDE

[75] Inventors: Sumio Umemura; Kyoji Ohdan; Fumihiko Sakai; Yasuo Bando; Harumi Ikezawa, all of Ube, Japan

[73] Assignee: Ube Industries, Ltd., Yamaguchi, Japan

[21] Appl. No.: 902,935

[22] Filed: May 5, 1978

Related U.S. Application Data

[60] Division of Ser. No. 816,916, Jul. 19, 1977, Pat. No. 4,110,350, which is a continuation of Ser. No. 623,448, Oct. 17, 1975, abandoned.

[30] Foreign Application Priority Data

Oct. 22, 1974 [JP] Japan .................................. 49-121009
Jul. 1, 1975 [JP] Japan .................................. 50-80527

[51] Int. Cl.² .................................................. B01J 27/14
[52] U.S. Cl. ........................................ 252/435; 252/437
[58] Field of Search ................................. 252/435, 437

[56] References Cited
U.S. PATENT DOCUMENTS

| | | | |
|---|---|---|---|
| 3,086,026 | 4/1963 | Wiefusch | 252/435 X |
| 3,156,705 | 11/1964 | Kerr | 252/435 X |
| 3,684,741 | 8/1972 | Friedichsen et al. | 252/437 X |
| 3,865,873 | 2/1975 | Oda et al. | 252/437 X |
| 3,875,220 | 4/1975 | White et al. | 252/437 X |
| 4,006,167 | 2/1977 | Umemura et al. | 252/435 X |
| 4,092,332 | 5/1978 | Freerks | 252/437 X |

Primary Examiner—Delbert E. Gantz
Assistant Examiner—William G. Wright
Attorney, Agent, or Firm—Miller & Prestia

[57] ABSTRACT

Unsaturated hydrocarbons having 4 to 6 carbon atoms are catalytically oxidized into maleic anhydride by using a catalyst, which consists essentially of oxides of (A) vanadium, (B) phosphorus, (C) titanium and (D) optionally at least one element selected from sodium, calcium, magnesium, iron, zirconium, boron, manganese, silver and molybdenum in the atomic ratios defined by the following formula $$VP_aTi_bX_cO_d$$

wherein X is the element (D) set forth above and a=1.0 to 5.0, b=2.0 to 12.0 and c=0 to 1.0, and which catalyst is prepared by calcining a mixture of a vanadium-containing compound and titanium dioxide at a temperature of 650° C. to 1,500° C., incorporating into the mixture a phosphorus-containing compound and optionally the element "X"-containing compound and, then, heating the resulting mixture.

15 Claims, No Drawings

CATALYTIC OXIDATIVE PROCESS FOR PRODUCING MALEIC ANHYDRIDE

This is a division, of application Ser. No. 816,916, filed July 19, 1977, now U.S. Pat. No., 4,110,350, which, in turn, is a continuation of U.S. application Ser. No. 623,448 filed Oct. 17, 1975, now abandoned, of common inventorship and assignment herewith.

This invention relates to a process for producing maleic anhydride by contacting in the vapor phase a feed mixture comprising an unsaturated hydrocarbon having 4 to 6 carbon atoms and oxygen with a catalyst exhibiting an improved activity.

Many proposals have been heretofore put forth for the production of maleic anhydride, which comprise catalytically oxidizing an unsaturated hydrocarbon having four to six carbon atoms such as n-butene, 1,3-butadiene, benzene or cyclopentadiene or a hydrocarbon mixture containing such an unsaturated hydrocarbon having 4 to 6 carbon atoms. Some typical processes have been carried out using a catalyst consisting of oxides of vanadium, phosphorus and titanium. For example, Japanese Patent Publication No. 7888/1965 discloses catalysts which consist of a vanadium oxide and a phosphorus oxide, the substantial part of said vanadium having a valency of less than 5. It is mentioned that these catalysts optionally contain as a cocatalyst a minor amount of another metal oxide such as an oxide of titanium, chromium, cobalt, nickel, zinc, zirconium, tin, antimony, bismuth or thorium.

Japanese Patent Publication No. 7737/1962 discloses a catalyst comprising anatase-type titanium dioxide particles covered with vanadium pentoxide or a mixture of vanadium pentoxide and potassium sulfate. Japanese Patent Publication No. 39845/1971 discloses a catalyst consisting essentially of vanadium pentoxide, titanium dioxide and at least one oxide or another compound of aluminum, lithium and zirconium. Japanese Patent Laid-open Application No. 62719/1973 discloses a catalyst consisting of vanadium pentoxide, phosphorus pentoxide, anatase-type titanium dioxide and optionally tungsten trioxide and/or molybdenum trioxide. It is to be noted that titanium dioxide present in these catalysts is of an anatase-type structure.

The above-mentioned known catalysts are not satisfactory because the yield of or selectivity to maleic anhydride is not attractive.

A main object of the present invention is to provide a process for effecting vapor phase oxidation of an unsaturated hydrocarbon having 4 to 6 carbon atoms, which makes it possible to produce maleic anhydride with improved yield.

Another object of the present invention is to provide a catalyst exhibiting improved activity for the vapor phase oxidation of an unsaturated hydrocarbon having 4 to 6 carbon atoms into maleic anhydride.

These and other objects and advantages of the present invention will become clear from the following description.

In accordance with the present invention, there is provided a process for producing maleic anhydride by catalytic oxidation of an unsaturated hydrocarbon having 4 to 6 carbon atoms, which comprises contacting a feed-gas mixture comprising said unsaturated hydrocarbon and oxygen in the vapor phase with a catalyst consisting essentially of oxides of (A) vanadium, (B) phosphorus, (C) titanium and (D) at least one element selected from the group consisting of sodium, calcium, magnesium, iron, zirconium, boron, manganese, silver and molybdenum, in the atomic ratios defined by the following formula $$VP_a Ti_b X_c O_d$$

wherein X is at least one element selected from the above group, and each of a, b and c is a positive number indicating an atomic ratio of each of the (B), (C) and (D) to vanadium and falling within the following ranges, a=1.0 to 5.0, preferably 2.0 to 4.0, b=2.0 to 12.0, preferably 4.5 to 10.0, and c=0 to 1.0, preferably 0.05 to 1.0, and d is a positive number satisfying the average valency of the (A), (B), (C) and (D), and being within the range from 8 to 40; said catalyst being prepared by calcining a mixture of a vanadium-containing compound and titanium dioxide at a temperature of 650° C. to 1,500° C., incorporating into the mixture a phosphorus-containing compound and optionally a compound containing the element "X" set forth above and, then, heating the resulting mixture.

The catalyst used in the process of the invention is characterized as, first, possessing a composition such that the respective components (A), (B), (C) and (D), set forth above, are present therein in the atomic ratios defined by the above formula, and; second, being prepared by the process comprising calcining a mixture of a vanadium-containing compound and titanium dioxide at a temperature of 650° C. to 1,500° C., incorporating into the mixture a phosphorus-containing compound and optionally a compound containing the element "X" set forth above and, then, heating the resulting mixture.

The amount of phosphorus present in the catalyst should be such that the atomic ratio of phosphorus to vanadium falls within the range of 1.0 to 5.0, preferably 2.0 to 4.0. The selectivity to maleic anhydride increases with an increase of the atomic ratio (P/V) of phosphorus to vanadium, but steeply decreases when the atomic ratio (P/V) exceeds approximately 5.0. The catalyst activity increases gradually with a decrease of the atomic ratio P/V, but maleic anhydride produced is undesirably oxidatively decomposed and the selectivity to maleic anhydride decreases when the atomic ratio P/V becomes lower than approximately 1.0. The amount of titanium should be such that the atomic ratio (Ti/V) of titanium to vanadium falls within the range of 2.0 to 12.0, preferably 4.5 to 10.0. The catalyst activity decreases with an increase of the atomic ratio (Ti/V) of titanium to vanadium and the yield of maleic anhydride decreases steeply when the atomic ratio (Ti/V) exceeds approximately 12.0. The yield of maleic anhydride becomes low also when the atomic ratio (Ti/V) is lower than approximately 2.0.

The atomic ratio (X/V) of the element "X" to vanadium may be varied within the range of 0 to 1.0, preferably 0.05 to 1.0. The incorporation of the element "X" is optional. However, it is advantageous to use a minor amount of the element "X", because the reaction temperature at which maleic anhydride is obtained with the maximum yield, i.e. the lowest reaction temperature at which the conversion of the unsaturated hydrocarbon is 100%, can be lowered thereby without the reduction in yield of maleic anhydride. The low reaction temperature is advantageous in that undesirable thermal decomposition is suppressed and it is easy to precisely control the reaction temperature. However, when the atomic ratio (X/V) is in excess of approximately 1.0, the yield of maleic anhydride decreases to an appreciable extent.

The process whereby the catalyst of the invention is prepared is critical. That is, a mixture of a vanadium-containing compound and titanium dioxide should be calcined at a temperature of 650° C. to 1,500° C. prior to incorporation of a phosphorus-containing compound and an optional element X-containing compound. The calcination of the aforesaid mixture is preferably carried out at 650° to 1,100° C., more preferably 650° to 900° C. The period of time for the calcination may be 30 minutes to several hours, usually 30 minutes to 2 hours.

The titanium dioxide to be blended with a vanadium-containing compound may be either of an anatase-type structure or of a rutile-type structure. The structure of titanium dioxide present in the calcined mixture is rutile whether it is anatase or rutile before the calcination. That is, when anatase titanium dioxide is calcined at the aforesaid temperature, it is converted to rutile-type titanium dioxide. It can readily be recognized by X-ray diffractiometry whether the structure of titanium dioxide is anatase or rutile. It is to be noted that anatase-type titanium oxide can readily be converted to rutile-type titanium dioxide even at a temperature on the order of 650° C. or so in the presence of a vanadium-containing compound, although it is known that anatase-type titanium dioxide can be converted to rutile at approximately 900° C. or more in the absence of a vanadium-containing compound. It should be especially noted that the catalyst of the present invention exhibits improved yield of maleic anhydride as compared with a catalyst prepared by a procedure similar to that defined in the present invention except that the calcination is carried out at a temperature lower than 650° C.

When the calcination at a temperature of 650° C. to 1,500° C. is carried out after blending the mixture of a vanadium-containing compound and titanium dioxide with a phosphorus-containing compound and optionally an element X-containing compound, it becomes difficult to obtain the desired catalyst because the phosphorus sublimes and flies away to some extent.

The mixture of a vanadium-containing compound and titanium dioxide may be prepared in a known manner, for example, by a wet process wherein a vanadium compound and a titanium dioxide are mixed with each other together with water followed by drying or a dry process wherein the two finely divided materials are blended with each other without water.

The compounds for the preparation of the catalyst may be oxides, acids or salts, or a mixture thereof. Illustrations of the vanadium-containing compounds are oxides such as vanadium pentoxide, vanadium trioxide, vanadium dioxide, vanadium monoxide and metavanadic acid; and salts such as vanadous chloride, vanadic chloride, vanadium tetrachloride, vanadium oxychloride and ammonium metavanadate. Of these compounds, vanadium pentoxide and ammonium metavanadate are preferable. Particularly vandadium pentoxide is optimum because weight loss is low and no toxic gas evolves when calcined.

Illustrations of the phosphorus-containing compounds are oxides such as phosphorus pentoxide, phosphorus tetraoxide and phosphorus trioxide; phosphates such as ammonium phosphate; and acid such as orthophosphoric acid and triphosphoric acid.

Illustrations of the element "X"-containing compounds are, for sodium-containing compounds, sodium oxide, sodium hydroxide, sodium nitrate, sodium sulfate and sodium carbonate; for calcium-containing compounds, calcium oxide, calcium hydroxide, calcium nitrate, calcium sulfate, calcium carbonate and calcium oxalate; for magnesium-containing compounds, magnesium oxide, magnesium hydroxide, magnesium nitrate, magnesium sulfate and magnesium carbonate; for iron-containing compounds, ferric oxide, ferrosoferric oxide, ferrous hydroxide, ferric hydroxide, ferrous nitrate, ferric nitrate and ferrous sulfate; for zirconium-containing compounds, zirconium oxide, zirconium nitrate, zirconyl nitrate [$ZrO(NO_3)_2$] and zirconium sulfate; for boron-containing compounds, boron trioxide and boric acid; for manganese-containing compounds, manganese dioxide, manganese nitrate, manganese carbonate and manganese oxalate; for silver-containing compounds, silver oxide, silver nitrate and silver carbonate; and, for molybdenum-containing componunds, molybdenum dioxide, molybdenum oxide and ammonium molybdate [$(NH_4)MoO_4$ and $(NH_4)_6Mo_7O_{24}$].

The materials, i.e. (1) the calcined mixture of the vanadium-containing compound and titanium dioxide, (2) the phosphorus-containing compound, and (3) the optional element "X"-containing compound, may be blended in a known manner; for example, by a wet process wherein the above three materials are mixed with each other in the form of solution and/or dispersion in a solvent, followed by removal of the solvent, or by a dry process wherein the above three materials are mixed with each other without use of the solvent. The prepared mixture of the above three materials is then heated generally at a temperature of 300° C. to 600° C., preferably 400° C. to 600° C. and for a period of 1 to 10 hours to obtain a catalyst. The catalyst is very hard. The catalyst may be pulverized and shaped into pellets or particles of desired shape and size. Alternatively, the mixture of the above three materials may be pulverized and/or shaped into pellets or particles of desired shape and size prior to the heating.

Unsaturated hydrocarbons having four to six carbon atoms which are used as a starting material in the process of the invention include, for example, aliphatic unsaturated hydrocarbons such as n-butene-1, n-butene-2 and 1,3-butadiene; alicyclic unsaturated hydrocarbons such as cyclopentadiene; and benzene. Of these, aliphatic straight chain unsaturated hydrocarbons are preferable. The unsaturated hydrocarbon used may be a hydrocarbon mixture containing at least approximately 20% by mole, preferably at least approximately 40% by mole, of one or more of the aforesaid unsaturated hydrocarbons of four to six carbon atoms. Suitable mixtures include, for example, a $C_4$-fraction produced in the course of catalytical cracking of petroleum naphtha, and a butane-butene fraction (B-B fraction) or spent B-B, i.e. a residue produced when 1,3-butadiene is extracted from the $C_4$-fraction.

As a source of oxygen which is used in the catalytic oxidation reaction of the invention, pure oxygen and an oxygen-containing gas such as air may be used. Particularly, air may be advantageously used. A relative proportion of oxygen in the feed-gas mixture is suitably from about 10 to about 200 moles per mole of the unsaturated hydrocarbon. In general, the unsaturated hydrocarbon and oxygen is diluted with an inert diluent gas such as nitrogen in order to avoid the risk of explosion. For example, the unsaturated hydrocarbon is advantageously diluted so that the resulting feed mixture contains 2% by volume or less preferably 0.1 to 1.5% by volume, of the unsaturated hydrocarbon.

Although the optimum reaction temperature varies to some extent depending upon the composition of the catalyst employed, the reaction temperature may be varied perferably within the range of 330° C. to 475° C., more preferably 350° C. to 450° C. The contact time may be varied preferably within the range of 0.2 to 1.8 seconds, more preferably 0.3 to 1.5 second.

The catalyst may be used alone or in combination with any of the known carriers. As carriers, those which bring favorable effects for the reaction involved, such as silica, alumina, and alumina-silica, which have been deactivated by, e.g. heat-treatment, may suitably be employed. The catalyst may be employed in either a fluidized bed or a fixed bed.

In practice, high yields of maleic anhydride are obtained. Saturated acids such as acetic acid are produced only in trace amounts. No detectable amounts of aldehydes are produced. The invention is further illustrated by the following examples and comparative examles, which are for purposes of illustration only and should not be construed as limiting the invention in any sense. In these examples, conversion and yield were calculated by the following equations.

$$\% \text{ conversion} = \frac{\text{moles } UHC \text{ consumed}}{\text{moles } UHC \text{ fed}} \times 100$$

$$\% \text{ yield} = \frac{\text{moles } MA \text{ produced}}{\text{moles } UHC \text{ fed}} \times 100$$

where MA is maleic anhydride and UHC is the unsaturated hydrocarbon having 4 to 6 carbon atoms employed. The yield used herein means a one pass yield.

EXAMPLE 1

A mixture of 5.4 g of a finely divided vanadium pentoxide powder and 45 g of a finely divided anatase-type titanium dioxide powder was calcined at 700° C. for one hour, thereby to obtain a dark purple powder. To 50 g of the dark purple powder, 13.6 g of an aqueous orthophosphoric acid and a minor amount of water were added. The mixture was ground down by using a kneader, dried at 110° C. and, then, maintained at 500° C. in the air for 5 hours. The obtained lump was pulverized and dressed into 10 to 20 mesh.

The catalyst so prepared was dark purple and had a composition such that the atomic ratios of P/v and Ti/v were 2.0 and 9.5, respectively. The titanium oxide present in the catalyst proved by X-ray diffractiometry to be of a rutile-type structure.

A feed-mixture of 0.5% by volume of butene-1 and 99.5% by volume of air was passed through a reactor packed with the above-mentioned catalyst and maintained at 450° C. The contact time was 0.6 second. The conversion of butene-1 and the yield of maleic anhydride and saturated acids are shown in Table I, below.

EXAMPLES 2 THROUGH 4

Following the procedure set forth in Example 1, maleic anhydride was prepared wherein 1,3-butadiene (in Example 2) and a B-B fraction (in Examples 3 and 4) were separately used instead of butene-1. The B-B faction used had the following composition.

|  | (in % by mole) |
|---|---|
| Isobutane | 0.68 |
| n-Butane | 3.59 |
| Butene-1* | 11.04 |
| Isobutene | 27.15 |
| Butene-2* | 7.91 |
| 1,3-Butadiene* | 47.37 |

*Effective ingredients, the total amount of which is 66.32% by mole.

In Examples 3 and 4, the reaction temperature was 470° C. and 450° C., respectively, and the content of the B-B fraction in the feed mixture was 1.2% by mole and 0.5% by mole, respectively. All other conditions remained substantially the same. Results are shown in Table I, below.

EXAMPLES 5 and 6

Following the procedure set forth in Example 1, a catalyst was prepared wherein rutile-type titanium dioxide was used instead of anatase-type titanium dioxide, with all other conditions remaining substantially the same.

Using the aforesaid catalyst, maleic anhydride was prepared from butene-1 (in Example 5) and 1,3-butadiene (in Example 6), respectively, under conditions similar to those employed in Example 1. Results are shown in Table I, below.

EXAMPLES 7 AND 8

7.7 g of ammonium metavanadate were added to 200 ml of water and, while being stirred, heated to dissolve the metavanadate in water. To the aqueous solution, 12.4 g of oxalic acid were added, thereby to reduce the vanadium and, then, 50 g of anatase-type titanium dioxide were added. The mixture was evaporated to dryness by heating it in a water bath. The dried product was calcined at 700° C. in the air for one hour to obtain a dark purple powder. To 45 g of this powder, 13.7 g of an aqueous orthophosphoric acid and minor amount of water were added. The mixture was ground down by using a kneader, dried at 110° C., and, then, maintained at 500° C. in the air for 5 hours. The catalyst so prepared had a composition such that the atomic ratios of P/v and Ti/v were 2.0 and 9.5, respectively.

Using the aforesaid catalyst, maleic anhydride was prepared from butene-1 (in Example 7) and 1,3-butadiene (in Example 8), respectively, under conditions similar to those employed in Example 1. Results are shown in Table I, below.

EXAMPLES 9 AND 10

Following the procedure set forth in Examples 7 and 8, a catalyst was prepared wherein rutile-type titanium dioxide was used instead of anatase-type titanium dioxide, with all other conditions remaining substantially the same.

Using the aforesaid catalyst, maleic anhydride was prepared from butene-1 (in Example 9) and 1,3-butadiene (in Example 10), respectively, under conditions similar to those employed in Example 1. Results are shown in Table I, below.

COMPARATIVE EXAMPLES 1 AND 2

These comparative examples illustrate the use of a catalyst prepared by calcining a mixture of vandium pentoxide and anatase-type titanium dioxide at a temperature lower than the claimed range.

Following the procedure set forth in Example 1, a catalyst was prepared wherein the mixture of vanadium pentoxide and anatase-type titanium dioxide was calcined at 600° C. instead of 700° C. with all other conditions remaining substantially the same. The catalyst so prepared was grayish green, and the titanium dioxide present therein proved by X-ray diffractiometry to be of an anatase-type structure.

Using the aforesaid catalyst, maleic anhydride was prepared from butene-1 (in Comparative Example 1) and 1,3-butadiene (in Comparative Example 2), respectively, under substantially the same conditions as those in Example 1 except that the reaction temperature was varied to 425° C. Results are shown in Table I, below.

COMPARATIVE EXAMPLES 3 AND 4

These comparative examples illustrate the use of a catalyst prepared by calcining of a vanadium pentoxide and rutile-type titanium dioxide mixture at a temperature lower than the claimed range.

Following the procedure set forth in Comparative Example 1, a catalyst was prepared wherein rutile-type titanium dioxide was used instead of anatase-type titanium dioxide, with all other conditions remaining substantially the same.

Using the aforesaid catalyst, maleic anhydride was prepared from butene-1 (in Comparative Example 3) and 1,3-butadiene (in Comparative Example 4), respectively, under conditions similar to those employed in Comparative Example 1. Results are shown in Table I, below.

COMPARATIVE EXAMPLE 5

This comparative example illustrates the use of a catalyst prepared without calcination of a mixture of vanadium pentoxide and anatase-type titanium dioxide.

Following the procedure set forth in Example 1, a catalyst was prepared wherein the mixture of vanadium pentoxide and anatase-type titanium dioxide was not calcined with all other conditions remaining substantially the same.

Using the aforesaid catalyst, maleic anhydride was prepared from a B-B fraction similar to that used in Examples 3 and 4 under substantially the same conditions as those in Example 1, except that the content of the B-B fraction in the feed mixture was 1.2% by volume. Results are shown in Table I, below.

COMPARATIVE EXAMPLES 6 AND 7

These comparative examples illustrate the use of a catalyst prepared from a mixture of vanadium pentoxide and rutile-type titanium dioxide without calcination of the mixture.

Following the procedure set forth in Example 1, a catalyst was prepared wherein rutile-type titanium dioxide was used instead of anatase-type titanium dioxide and the calcination at 700° C. of the mixture of rutile-type titanium dioxide and vanadium pentoxide was not carried out, with all other conditions remaining substantially the same.

Using the catalyst so prepared, maleic anhydride was prepared from butene-1 (in Comparative Example 6) and 1,3-butadiene (in Comparative Example 7) in a manner similar to that in Example 1, except that the reaction temperature was varied to 425° C. Results are shown in Table I, below.

EXAMPLES 11 AND 12

These examples illustrate the use of a catalyst prepared by calcining a mixture of vanadium pentoxide and anatase-type titanium dioxide at a varied temperature.

Following the procedure set forth in Example 1, a catalyst was prepared wherein the mixture of vanadium pentoxide and anatase-type $TiO_2$ was calcined at 650° C. (in Example 11) and 750° C. (in Example 12) instead of 700° C., with all other conditions remaining substantially the same.

Using the catalyst so prepared, maleic anhydride was prepared in a manner similar to that in Example 1, except that 1,3-butadiene was used instead of butene-1. Results are shown in Table I, below.

COMPARATIVE EXAMPLES 8 AND 9

These comparative examples illustrate the use of a catalyst prepared by using a reduced vanadium and not calcining the mixture of the vanadium oxide and anatase-type titanium dioxide.

7.7 g of ammonium metavanadate were added to 200 ml of water and, while being stirred, and the mixture was heated to dissolve the metavanadate in the water. To the aqueous solution, 12.4 g of oxalic acid were added to thereby reduce the vanadium and, then, 15.2 g of an aqueous 85% orthophosphoric acid and 50 g of anatase-type titanium dioxide were added. The mixture was graduated by heating to obtain a paste. The paste was dried at 110° C., and, then, maintained at 500° C. in the air for 5 hours.

The catalyst so prepared was grayish green and had a composition such that the atomic ratios of P/V and Ti/V were 2.0 and 9.5, respectively. The titanium oxide present in the catalyst proved by X-ray diffractiometry to be of an anatase structure.

Using the aforesaid catalyst, maleic anhydride was prepared from butene-1 (in Comparative Example 8) and 1,3-butadiene (in Comparative Example 9) under substantially the same conditions as those in Example 1, except that the reaction temperature was 425° C. Results are shown in Table I.

Table 1

| Example No. | Hydrocarbon fed | Calcination temperature (°C.) | Reaction temperature (°C.) | Conversion (%) | Yield Maleic anhydride (%) | Yield Saturated acids (%) |
|---|---|---|---|---|---|---|
| 1 | Butene-1 | 700 | 450 | 100 | 55.2 | 1.8 |
| 2 | 1,3-Butadiene | 700 | 450 | 100 | 66.8 | 0.8 |
| 3 | B-B fraction | 700 | 470 | 96.4 | 36.7 (55.7*) | 2.0 |
| 4 | B-B fraction | 700 | 450 | 96.3 | 39.3 (59.3*) | 2.2 |
| 5 | Butene-1 | 700 | 450 | 100 | 55.0 | 1.9 |
| 6 | 1,3-Butadiene | 700 | 450 | 100 | 65.5 | 0.8 |
| 7 | Butene-1 | 700 | 450 | 100 | 56.0 | 1.8 |
| 8 | 1,3-Butadiene | 700 | 450 | 100 | 66.4 | 0.6 |
| 9 | Butene-1 | 700 | 450 | 100 | 54.2 | 1.8 |

Table 1-continued

| Example No. | Hydrocarbon fed | Calcination temperature (°C.) | Reaction temperature (°C.) | Conversion (%) | Yield Maleic anhydride (%) | Yield Saturated acids (%) |
|---|---|---|---|---|---|---|
| 10 | 1,3-Butadiene | 700 | 450 | 100 | 64.8 | 0.8 |
| 11 | 1,3-Butadiene | 650 | 450 | 100 | 66.0 | 0.8 |
| 12 | 1,3-Butadiene | 750 | 450 | 100 | 65.8 | 0.8 |
| Com. 1 | Butene-1 | 600 | 425 | 100 | 48.0 | 1.0 |
| Com. 2 | 1,3-Butadiene | 600 | 425 | 100 | 58.0 | 0.8 |
| Com. 3 | Butene-1 | 600 | 425 | 100 | 48.6 | 1.9 |
| Com. 4 | 1,3-Butadiene | 600 | 425 | 100 | 58.1 | 0.8 |
| Com. 5 | B-B fraction | — | 450 | 96.1 | 29.0 (43.7*) | 2.0 |
| Com. 6 | Butene-1 | — | 425 | 100 | 48.3 | 1.2 |
| Com. 7 | 1,3-Butadiene | — | 425 | 100 | 58.1 | 0.9 |
| Com. 8 | Butene-1 | — | 425 | 100 | 50 | 1.2 |
| Com. 9 | 1,3-Butadiene | — | 425 | 100 | 59.9 | 0.8 |

*Yield calculated based on the total amount of the effective ingredients present in the B-B fraction.

EXAMPLES 13 THROUGH 16 AND COMPARATIVE EXAMPLES 10 THROUGH 14

These examples and comparative examples illustrate the use of catalysts containing V, P and Ti in various amounts.

Following the procedure set forth in Example 1, catalysts were prepared wherein the amounts of anatase-type titanium dioxide and orthophosphoric acid were varied, with all other conditions remaining substantially the same. The catalysts so prepared had the compositions shown in Table II, below. The titanium oxide present in the catalysts was all of a rutile-type structure.

Using each of the aforesaid catalysts, maleic anhydride was prepared in a manner similar to that set forth in Example 1, except that 1,3-butadiene was used instead of butene-1 and the reaction temperature was varied as shown in Table II. Results are shown in Table II.

Table II

| Example No. | Atomic ratio V | Atomic ratio P | Atomic ratio Ti | Reaction temp. (°C.) | Conversion (%) | Yield Maleic anhydride (%) | Yield Saturated acids (%) |
|---|---|---|---|---|---|---|---|
| 13 | 1 | 1 | 9.5 | 425 | 100 | 62.4 | 0.2 |
| 14 | 1 | 5 | 9.5 | 450 | 100 | 66.0 | 0.8 |
| 15 | 1 | 2 | 2 | 450 | 100 | 63.2 | 0.8 |
| 16 | 1 | 2 | 12 | 450 | 100 | 65.0 | 0.7 |
| Com. 10 | 1 | 0.5 | 9.5 | 350 | 100 | 30.2 | 0.2 |
| Com. 11 | 1 | 0.5 | 9.5 | 450 | 100 | 25.0 | 0.1 |
| Com. 12 | 1 | 6 | 9.5 | 475 | 100 | 55.3 | 2.0 |
| Com. 13 | 1 | 2 | 1 | 425 | 100 | 50.3 | 1.0 |
| Com. 14 | 1 | 2 | 13 | 450 | 98 | 50.0 | 1.0 |

EXAMPLES 17 THROUGH 28

These examples illustrate the use of catalysts containing V, P, Ti and another metal (X).

Following the procedure set forth in Example 1, catalysts were prepared wherein various metal (X)-containing compounds shown in Table III, below, were separately added together with the aqueous 85% orthophosphoric acid to the calcined mixture of vanadium pentoxide and titanium dioxide, with all other conditions remaining substantially the same.

Each catalyst was dark purple and had a composition such that the atomic ratios of P/V, Ti/V and X/V were 2.0, 9.5 and 0.1, respectively. The titanium dioxide present in each catalyst proved by x-ray diffractiometry to be of a rutile-type structure.

Using each catalyst, maleic anhydride was prepared from butene-1 (in Examples 17 through 27) and 1,3-butadiene (in Example 28) under substantially the same conditions as those in Example 1, except that the reaction temperature was varied as shown in Table III. Results are shown in Table III. In each Example, the yield of saturated acids was only below 2% and aldehydes were produced only in trace amounts. The conversion of butene-1 and 1,3-butadiene was 100% in Examples 18 through 28 and 95% in Example 17.

Table III

| Ex. No. | X | Metal (X)-containing compound | amount used (g) | Reaction temp. (°C.) | Yield of maleic anhydride (%) |
|---|---|---|---|---|---|
| 17 | Na | NaNO$_3$ | 0.5 | 400 | 53.0 |
| 18 | Na | NaNO$_3$ | 0.5 | 425 | 55.8 |
| 19 | Na | NaNO$_3$ | 0.5 | 450 | 54.0 |
| 20 | Ca | Ca(NO$_3$)$_2$ . 4H$_2$O | 1.39 | 425 | 55.2 |
| 21 | Mg | Mg(NO$_3$)$_2$ . 6H$_2$O | 1.51 | 425 | 58.0 |
| 22 | Fe | Fe(NO$_3$)$_2$ . 6H$_2$O | 1.69 | 425 | 55.5 |
| 23 | Zr | ZrO(NO$_3$)$_2$ . 2H$_2$O | 1.57 | 400 | 55.0 |
| 24 | B | H$_3$BO$_3$ | 0.36 | 425 | 55.9 |
| 25 | Mn | Mn(NO$_3$)$_2$ . 6H$_2$O | 1.69 | 425 | 56.1 |
| 26 | Ag | AgNO$_3$ | 1.00 | 425 | 55.1 |
| 27 | Mo | (NH$_4$)$_6$Mo$_7$O$_{24}$ . 4H$_2$O | 1.05 | 425 | 54.9 |
| 28 | Na | NaNO$_3$ | 0.5 | 425 | 68.0 |

COMPARATIVE EXAMPLE 15

Following the procedure set forth in Examples 17 through 28, a catalyst was prepared wherein the mixture of vanadium pentoxide and anatase-type titanium dioxide was calcined at 600° C. instead of 700° C. with all other conditions remaining substantially the same. The titanium dioxide present in the catalyst so prepared proved by X-ray diffractiometry to be of an anatase-type structure.

Using the aforesaid catalyst, maleic anhydride was prepared from butene-1 in a manner similar to that in Example 18. The conversion of butene-1 was 100% and the yield of maleic anhydride was only 48%.

What we claim is:

1. Catalyst composition consisting essentially of oxides defined by the following formula:

VP$_a$Ti$_b$X$_c$O$_d$ wherein said oxides of titanium and vanadium are the product of calcining a mixture of a vanadium-containing compound and titanium dioxide at a temperature of 650° to 1500° C., X is at least one element selected from the group consisting of sodium, calcium, magnesium, iron, zirconium, boron, manganese, silver and molybdenum, and "a" is 1.0 to 5.0, "b" is 2.0 to 12.0, "c" is 0 to 1.0, and "d" is a number within the range of 8 to 40 satisfying the average valency of the vanadium, phosphorous, titanium and X, wherein after calcining said titanium dioxide is rutile titanium dioxide.

2. Catalyst composition as recited in claim 1 wherein a=2.0 to 4.0, b=4.5 to 10.0, and c=0.05 to 1.0.

3. Catalyst composition as recited in claim 1 wherein said composition includes a catalyst carrier.

4. Catalyst composition as recited in claim 1 wherein a=2.0 to 4.0, b=4.5 to 10.0 and c=0.

5. Method of preparation of a catalyst, said catalyst having a composition defined by the following formula:

$$VP_aTi_bX_cO_d$$

wherein X is at least one element selected from the group consisting of sodium, calcium, magnesium, iron, zirconium, boron, manganese, silver and molybdenum, and "a" is 1.0 to 5.0, "b" is 2.0 to 12.0, "c" is 0 to 1.0, and "d" is a number within the range of 8 to 40 satisfying the average valency of the vanadium, phosphorous, titanium and X, said titanium oxide being rutile titanium dioxide, said method comprising the steps of calcining a mixture of a vanadium-containing compound and titanium dioxide at a temperature of 650° C. to 1,500° C., incorporating into the calcined mixture a phosphorus-containing compound or both a phosphorus-containing compound and a compound containing the element "X" set forth above and, then, heating the resulting mixture at a temperature of 300° C. to 600° C.

6. Method as recited in claim 5, wherein said resulting mixture is heated to 450°–600° C.

7. Method as recited in claim 5, wherein said phosphorus-containing compound is a phosphorus-containing oxide, acid or salt.

8. Method as recited in claim 5, wherein said phosphorus-containing compound is phosphorus pentoxide, phosphorus tetraoxide, phosphorus trioxide, ammonium phosphate, orthophosphoric acid or triphosphoric acid.

9. Method as recited in claim 5, wherein said calcination is carried out at 650°–1100° C.

10. Method as recited in claim 5, wherein said calcination is carried out at 650°–900° C.

11. Method as recited in claim 5, wherein said calcination is continued for at least 30 minutes.

12. Method as recited in claim 5, wherein said calcination is continued for a time in the range of ½ to 2 hours.

13. Method as recited in claim 6, wherein said vanadium-containing compound is vanadium oxide, acid or salt or a mixture thereof.

14. Method as recited in claim 6, wherein said vanadium-containing compound is selected from the group consisting of vanadium pentoxide, vanadium trioxide, vanadium dioxide, vanadium monoxide, metavanadic acid, vanadous chloride, vanadic chloride, vanadium tetrachloride, vanadium oxychloride and ammonium metavanadate.

15. Method as recited in claim 6, wherein said vanadium-containing compound is vanadium pentoxide or ammonium metavanadate.

* * * * *